(12) United States Patent
Sweeney et al.

(10) Patent No.: US 10,766,500 B2
(45) Date of Patent: *Sep. 8, 2020

(54) SENSORY STIMULATION SYSTEM FOR AN AUTONOMOUS VEHICLE

(71) Applicant: UATC, LLC, San Francisco, CA (US)

(72) Inventors: Matthew Sweeney, Boston, MA (US); Emily Bartel, Pittsburgh, PA (US)

(73) Assignee: UATC, LLC, San Francisco, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 16/051,910

(22) Filed: Aug. 1, 2018

(65) Prior Publication Data

US 2018/0339715 A1 Nov. 29, 2018

Related U.S. Application Data

(63) Continuation of application No. 15/651,878, filed on Jul. 17, 2017, now Pat. No. 10,112,623, which is a
(Continued)

(51) Int. Cl.
| | |
|---|---|
| *B60W 50/16* | (2020.01) |
| *B60N 2/18* | (2006.01) |
| *G05D 1/02* | (2020.01) |
| *A61M 21/00* | (2006.01) |
| *B60H 1/00* | (2006.01) |

(Continued)

(52) U.S. Cl.
CPC ............ *B60W 50/16* (2013.01); *A61M 21/00* (2013.01); *B60H 1/00764* (2013.01); *B60N 2/0244* (2013.01); *B60N 2/14* (2013.01); *B60N 2/185* (2013.01); *B60R 1/00* (2013.01); *B60W 40/10* (2013.01); *G05D 1/02* (2013.01); *A61M 2021/0022* (2013.01); *A61M 2021/0027* (2013.01); *A61M 2021/0044* (2013.01); *A61M 2205/332* (2013.01); *B60N 2002/981* (2018.02);
(Continued)

(58) Field of Classification Search
USPC .......................................................... 701/23
See application file for complete search history.

(56) References Cited

U.S. PATENT DOCUMENTS 6,424,410 B1 7/2002 Pelosi
8,996,224 B1 3/2015 Herback
(Continued)

FOREIGN PATENT DOCUMENTS

| CN | 103150698 | 6/2012 |
|---|---|---|
| CN | 103213534 | 7/2013 |
| WO | WO 2015/099679 | 7/2015 |

OTHER PUBLICATIONS

ISR and Written Opinion in PCT/US2017/023411 dated Jul. 13, 2017.
(Continued)

*Primary Examiner* — Tyler D Paige
(74) *Attorney, Agent, or Firm* — Dority & Manning, P.A.

(57) ABSTRACT

A sensory stimulation system within an interior of an autonomous vehicle (AV) can obtain maneuver data representing one or more maneuvers to be performed by the AV. For each respective maneuver of the one or more maneuvers, the system can determine one or more visual outputs to provide a passenger of the AV with a sensory indication of the respective maneuver, and then output the one or more visual outputs via the display system.

20 Claims, 7 Drawing Sheets

Related U.S. Application Data continuation of application No. 15/059,493, filed on Mar. 3, 2016, now Pat. No. 9,789,880.

(51) Int. Cl.
*B60W 40/10* (2012.01)
*B60N 2/02* (2006.01)
*B60R 1/00* (2006.01)
*B60N 2/14* (2006.01)
*B60N 2/90* (2018.01)

(52) U.S. Cl.
CPC ... *B60R 2300/207* (2013.01); *B60R 2300/302* (2013.01); *B60R 2300/607* (2013.01)

(56) References Cited

U.S. PATENT DOCUMENTS

| | | | |
|---|---|---|---|
| 9,171,268 B1 | 10/2015 | Penilla | |
| 9,335,764 B2 | 5/2016 | Herz | |
| 9,411,780 B1 | 8/2016 | Awad | |
| 9,440,605 B2 | 9/2016 | Vadgama | |
| 9,716,565 B2 | 7/2017 | Mandeville-Clarke | |
| 9,789,880 B2* | 10/2017 | Sweeney | B60W 50/16 |
| 9,827,811 B1* | 11/2017 | McNew | B60N 2/90 |
| 9,902,403 B2 | 2/2018 | Donnelly | |
| 10,112,623 B2* | 10/2018 | Sweeney | B60W 50/16 |
| 10,360,714 B1* | 7/2019 | Xue | G05D 1/0088 |
| 2005/0040573 A1 | 2/2005 | Bolt | |
| 2006/0045030 A1 | 3/2006 | Bieselin | |
| 2012/0131455 A1 | 5/2012 | Han | |
| 2013/0197674 A1 | 8/2013 | Lowry | |
| 2014/0218307 A1 | 8/2014 | Goldman-Shenhar | |
| 2014/0253722 A1 | 9/2014 | Smyth | |
| 2015/0084985 A1 | 3/2015 | Baudu | |
| 2015/0097864 A1 | 4/2015 | Alaniz | |
| 2015/0109131 A1 | 4/2015 | Lindberg | |
| 2015/0185034 A1 | 7/2015 | Abhyanker | |
| 2015/0338852 A1 | 11/2015 | Ramanujam | |
| 2015/0339928 A1 | 11/2015 | Ramanujam | |
| 2015/0346722 A1 | 12/2015 | Herz | |
| 2016/0001720 A1 | 1/2016 | Vadgama | |
| 2016/0318442 A1 | 11/2016 | James | |
| 2016/0330578 A1 | 11/2016 | Moussavian | |
| 2016/0347348 A1 | 12/2016 | Lubischer | |
| 2016/0358453 A1 | 12/2016 | Wassef | |
| 2017/0103571 A1 | 4/2017 | Beaurepaire | |
| 2017/0113702 A1 | 4/2017 | Thieberger-Navon | |
| 2017/0126810 A1 | 5/2017 | Kentley | |
| 2017/0132334 A1 | 5/2017 | Levinson | |
| 2017/0132769 A1 | 5/2017 | Barron | |
| 2017/0136842 A1 | 5/2017 | Anderson | |
| 2017/0151918 A1 | 6/2017 | Boesen | |
| 2017/0153319 A1 | 6/2017 | Villeneuve | |
| 2017/0153636 A1 | 6/2017 | Boesen | |
| 2017/0158023 A1 | 6/2017 | Stevanovic | |
| 2017/0253252 A1* | 9/2017 | Donnelly | B60W 50/0098 |
| 2017/0253254 A1* | 9/2017 | Sweeney | B60W 50/16 |
| 2017/0256229 A1 | 9/2017 | Kocharlakota | |
| 2017/0259059 A1* | 9/2017 | Medford | B60N 2/002 |
| 2017/0267254 A1* | 9/2017 | Leppanen | G06F 3/016 |
| 2017/0276494 A1 | 9/2017 | Kusano | |
| 2017/0277191 A1 | 9/2017 | Fairfield | |
| 2017/0291538 A1 | 10/2017 | Sivak | |
| 2017/0313326 A1* | 11/2017 | Sweeney | B60W 50/16 |
| 2017/0371334 A1* | 12/2017 | Nagy | B60W 50/14 |
| 2018/0040162 A1 | 2/2018 | Donnelly | |
| 2018/0040163 A1 | 2/2018 | Donnelly | |
| 2018/0086344 A1 | 3/2018 | Zhu | |
| 2018/0089901 A1 | 3/2018 | Rober | |
| 2018/0339715 A1* | 11/2018 | Sweeney | B60W 50/16 |

OTHER PUBLICATIONS

Gervautz, et al. Anywhere Interfaces Using Handheld Augmented Reality, 2012, IEEE, p. 26-31.
Munoz, et al., PhysioVR: A Novel Mobile Virtual Reality Framework for Physiological Computing, 2016, IEEE, p. 1-6.
Brogan, et al., Dynamically Simulated Characters in Virtual Environments, 1998, IEEE, p. 58-69.
Rao, et al., AR-IVI—Implementation of In-Vehicle Augmented Reality, 2014, IEEE, p. 3-8.
Ai, et al. Real-Time Unmanned Aerial Vehicle 3D Environment Exploration in a Mixed Reality Environment, 2016, IEEE, p. 664-670.
Zhi-Hua, et al., Design of UAV Telepresence and Simulation Platform based on VR, 2008, IEEE, p. 520-524.
Santano, et al., Aerial Videography in Built-Heritage Documentation: The Case of Post-Independence Architeture of Malaysia, 2014, IEEE, p. 1-6.
Chae, et al., The Comparison of the Detecting Performance between the Ground and the Aerial Visual Analytics in the UGV-UAV Collaborative System, 2016, IEEE, p. 524-529.
Ai, et al., "Real-Time Unmanned Aerial Vehicle 3D Environment Exploration in a Mixed Reality Environment", International Conference on Unmanned Aircraft Systems, Jun. 7-10, 2016, pp. 664-670.
Brogan, et al, "Dynamically Simulated Characters in Virtual Environments", Animating Humans, Sep./Oct. 1998, 12 pages.
Chae et al, "The Comparison of the Detecting Performance between the Ground and the Aerial Visual Analytics in the UGV-UAV Collaborative System", International Conference on Advance Intelligent Mechatronics, Jul. 12-15, 2016, Banff, Alberta, Canada, pp. 524-529.
Examination Report for AU 2017241321, dated Sep. 25, 2018, 3 pages.
Examination Report for AU 2017241321, dated Jul. 26, 2019, 3 pages.
Gervautz, et al, "Anywhere Interfaces Using Handheld Augmented Reality", Computer, Jul. 2012, pp. 26-31.
International Search Report and Written Opinion for PCT/US2017/023411, dated Jul. 13, 2017, 9 pages.
Munoz, et al, "PhysioVR: A Novel Mobile Virtual Reality Framework for Physiological Computing", International Conference on e-Heajth Networking, Applications and Services, Sep. 14-17, 2016, Munich, Germany, 6 pages.
Rao et al, "AR-IVI—Implementation of In-Vehicle Augmented Reality", International Symposium on Mixed and Augmented Reality, Sep. 10-12, 2014, Munich, Germany, 6 pages.
Santano, et al, "Aerial Videography in Built-Heritage Documentation: The Case of Post-Independence Architecture of Malaysia", International Conference on Virtual Systems & Multimedia, Dec. 9-12, 2014, Hong Kong, 6 pages.
Zhi-hua et al, "Design of UAV Telepresence and Simulation Platform based on VR", International Conference on Cyberworlds, Sep. 22-24, 2008, Hangzhou, China. p. 520-524.

* cited by examiner

SENSORY STIMULATION SYSTEM FOR AN AUTONOMOUS VEHICLE

CROSS REFERENCE TO RELATED APPLICATIONS

This application is a continuation of U.S. patent application Ser. No. 15/651,878, titled "Sensory Stimulation System for an Autonomous Vehicle," and filed on Jul. 17, 2017, which is a continuation of U.S. patent application Ser. No. 15/059,493, also titled "Sensory Stimulation System for an Autonomous Vehicle," and filed on Mar. 3, 2016; the aforementioned priority applications being hereby incorporated by reference in their respective entireties.

BACKGROUND

With the advent of autonomous vehicle (AV) technology, rider attention may be focused on alternative activities, such as work, socializing, reading, writing, task-based activities (e.g., organization, bill payments, online shopping, gameplay), and the like. As the AV travels along an inputted route, kinetosis (i.e., motion sickness) can result from the perception of motion by a rider not corresponding to the rider's vestibular senses.

BRIEF DESCRIPTION OF THE DRAWINGS

The disclosure herein is illustrated by way of example, and not by way of limitation, in the figures of the accompanying drawings in which like reference numerals refer to similar elements, and in which.

DETAILED DESCRIPTION

Figure 1:
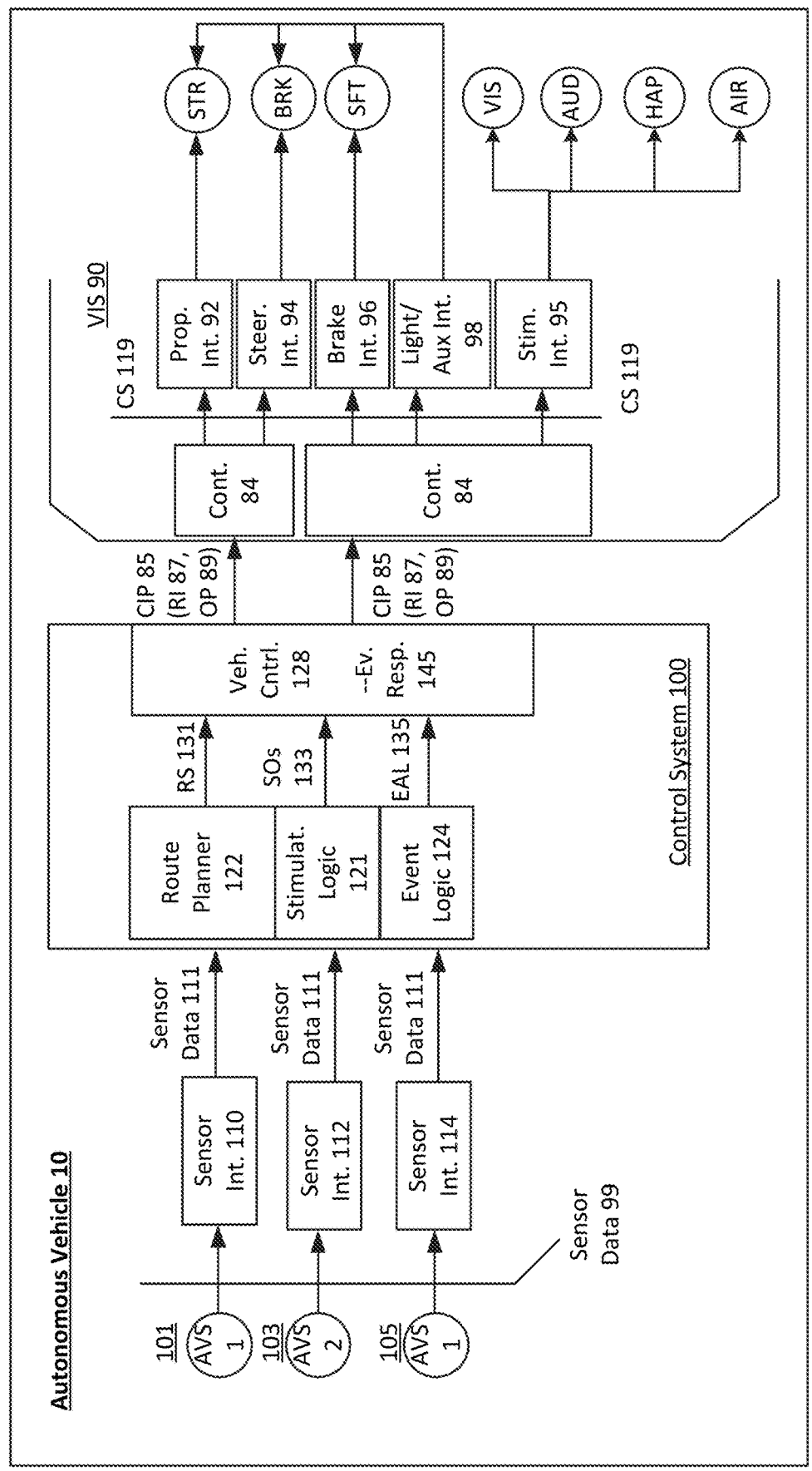
FIG. 1 is a block diagram illustrating an example control system for operating an autonomous vehicle including a sensory stimulation system, as described herein.

A sensory stimulation system is disclosed that provides sensory stimulation outputs responsive to or preemptive of maneuvers by the autonomous vehicle (AV). The sensory stimulation system can include a number of output devices to provide visual, audio, tactile, and/or any combination of vestibular stimulation for AV riders to counter, reactively and/or proactively, the sensory effects cause by AV motion that can potentially lead to kinetosis. In some examples, the sensory stimulation system can provide a sub-conscious or unconscious learning atmosphere within the passenger interior of the AV that can prevent motion sickness and/or provide preemptive feedback to riders such that habitual vestibular responses by the riders to outputted stimulations can be developed. Accordingly, such habitual vestibular responses can create a learned correlation between the rider's vestibular system (e.g., (i) the rider's semi-circular canal system which senses rotational movement and (ii) the rider's inner ear otoliths which indicate linear accelerations) and the rider's visual perception.

According to examples described herein, the sensory stimulation system can dynamically determine maneuvers to be performed by the AV. Such maneuvers can include acceleration, braking, or directional change maneuvers. In many aspects, the sensory stimulation system can receive inputs indicating the AV's current speed, a current route traveled by the AV, and an immediate action plan (e.g., indicating immediate actions to be performed by the AV, such as changing lanes or braking). Additionally or alternatively, the sensory stimulation system can include a number of sensors, such as an accelerometer and/or gyroscopic sensor, to reactively determine the maneuvers of the AV. For each maneuver, the sensory stimulation system can generate a set of sensory stimulation outputs to provide a rider of the AV with sensory indications of the maneuver, and output the set of sensory stimulation outputs via the output devices within the interior of the AV. In various implementations, the sensory stimulation outputs can be generated and outputted by the sensory stimulation system dynamically as the AV maneuvers along a current route to a destination.

In many examples, the output devices can include visually perceptive devices, such as a light bar visible within an interior of the AV. The light bar can be included to circumscribe at least a portion of the interior passenger compartment (e.g., around the ceiling of the interior, and/or around a mid-plane just below the windows) and can provide visual stimulation based on each acceleration, braking, or change of direction action performed by the AV, or combination thereof. The light bar can include multi-colored light elements which can be controlled by the sensory stimulation system to dynamically generate colors and brightness for respective portions of the light bar to indicate each of the maneuvers.

Additionally or alternatively, the output devices can include a number of display units visible within the interior of the AV. For example, one or more display units can be provided on the dashboard of the AV and behind the front seats to provide each passenger with a view of a particular display. In certain implementations, the sensory stimulation system can dynamically generate a displayed presentation that indicates the AV's planned actions. In some examples, the sensory stimulation system can generate a third-person perspective, visual representation of the AV traveling along a current route for display, and can further generate preemptive and/or dynamic visual indications of each maneuver to be performed by the AV. In some examples, the preemptive visual indications can have a granularity that aligns with decision-making performed by a control system of the AV, as described herein.

In many examples, the output devices can include controllable seats. The controllable seats can be operable by the sensory stimulation system and can include haptic functionality. Additionally or alternatively, each of the controllable seats can include a number of motors that can control pitch, roll, and/or yaw of the seat. As the AV travels along the current route, the sensory stimulation system can operate the controllable seats to provide haptic stimulation and/or control the principal axes (i.e., pitch, roll, yaw) of the seats based on the maneuvers of the AV.

Additionally or alternatively, the output devices of the sensory stimulation system can include an airflow system capable of providing air pressure outputs as sensory stimulations based on the maneuvers of the AV. The airflow system can include the AV's manufacturer installed air conditioning system and/or a customized air flow control system that can provide air flow stimulation to the riders from multiple directions and at differing intensities. For example, when the AV is about to brake, the sensory stimulation system can utilize the airflow system to modify airflow within the cabin (e.g., change from rearward airflow to forward airflow). Airflow adjustment parameters for the airflow system can include airflow speed/intensity, direction (e.g., 360 degrees around the riders both radially and azimuthally), temperature, timing, pulse rate, and height (e.g., aiming at the rider's head, shoulders, torso, arms, legs, feet, etc.). In some implementations, airflow outlets can be provided through the dashboard, the dashboard underside, the floor, the seats (e.g., through outlets on the headrest), or via ducting through the AV's chassis with outlets on the sideposts and/or doors.

Among other benefits, the examples described herein achieve a technical effect of providing sensory stimulation for AV riders based on the maneuvers of the AV. Such stimulation can train the sensory responses of riders to prevent kinetosis due to uncorrelated vestibular versus visual perception.

As used herein, a computing device refers to devices corresponding to desktop computers, cellular devices or smartphones, personal digital assistants (PDAs), laptop computers, tablet devices, television (IP Television), etc., that can provide network connectivity and processing resources for communicating with the system over a network. A computing device can also correspond to custom hardware, in-vehicle devices, or on-board computers, etc. The computing device can also operate a designated application configured to communicate with the network service.

One or more examples described herein provide that methods, techniques, and actions performed by a computing device are performed programmatically, or as a computer-implemented method. Programmatically, as used herein, means through the use of code or computer-executable instructions. These instructions can be stored in one or more memory resources of the computing device. A programmatically performed step may or may not be automatic.

One or more examples described herein can be implemented using programmatic modules, engines, or components. A programmatic module, engine, or component can include a program, a sub-routine, a portion of a program, or a software component or a hardware component capable of performing one or more stated tasks or functions. As used herein, a module or component can exist on a hardware component independently of other modules or components. Alternatively, a module or component can be a shared element or process of other modules, programs or machines.

Some examples described herein can generally require the use of computing devices, including processing and memory resources. For example, one or more examples described herein may be implemented, in whole or in part, on computing devices such as servers, desktop computers, cellular or smartphones, personal digital assistants (e.g., PDAs), laptop computers, printers, digital picture frames, network equipment (e.g., routers) and tablet devices. Memory, processing, and network resources may all be used in connection with the establishment, use, or performance of any example described herein (including with the performance of any method or with the implementation of any system).

Furthermore, one or more examples described herein may be implemented through the use of instructions that are executable by one or more processors. These instructions may be carried on a computer-readable medium. Machines shown or described with figures below provide examples of processing resources and computer-readable mediums on which instructions for implementing examples disclosed herein can be carried and/or executed. In particular, the numerous machines shown with examples of the invention include processors and various forms of memory for holding data and instructions. Examples of computer-readable mediums include permanent memory storage devices, such as hard drives on personal computers or servers. Other examples of computer storage mediums include portable storage units, such as CD or DVD units, flash memory (such as carried on smartphones, multifunctional devices or tablets), and magnetic memory. Computers, terminals, network enabled devices (e.g., mobile devices, such as cell phones) are all examples of machines and devices that utilize processors, memory, and instructions stored on computer-readable mediums. Additionally, examples may be implemented in the form of computer-programs, or a computer usable carrier medium capable of carrying such a program.

Numerous examples are referenced herein in context of an autonomous vehicle (AV). An AV refers to any vehicle which is operated in a state of automation with respect to steering and propulsion. Different levels of autonomy may exist with respect to AVs. For example, some vehicles may enable automation in limited scenarios, such as on highways, provided that drivers are present in the vehicle. More advanced AVs drive without any human assistance from within or external to the vehicle. Such vehicles often are required to make advance determinations regarding how the vehicle is behave given challenging surroundings of the vehicle environment.

System Description

FIG. 1 is a block diagram illustrating an example control system 100 for operating an autonomous vehicle (AV) 10 including a sensory stimulation system, as described herein. In an example of FIG. 1, a control system 100 can be used to autonomously operate the AV 10 in a given geographic region for a variety of purposes, including transport services (e.g., transport of humans, delivery services, etc.). In examples described, an autonomously driven vehicle can operate without human control. For example, in the context of automobiles, an autonomously driven vehicle can steer, accelerate, shift, brake and operate lighting components. Some variations also recognize that an autonomous-capable vehicle can be operated either autonomously or manually.

In one implementation, the control system 100 can utilize specific sensor resources in order to intelligently operate the vehicle 10 in most common driving situations. For example, the control system 100 can operate the vehicle 10 by autonomously steering, accelerating, and braking the vehicle 10 as the vehicle progresses to a destination. The control system 100 can perform vehicle control actions (e.g., braking, steering, accelerating) and route planning using sensor information, as well as other inputs (e.g., transmissions from remote or local human operators, network communication from other vehicles, etc.).

In an example of FIG. 1, the control system 100 includes a computer or processing system which operates to process sensor data that is obtained on the vehicle with respect to a road segment upon which the vehicle 10 operates. The sensor data can be used to determine actions which are to be performed by the vehicle 10 in order for the vehicle 10 to continue on a route to a destination. In some variations, the control system 100 can include other functionality, such as wireless communication capabilities, to send and/or receive wireless communications with one or more remote sources. In controlling the vehicle 10, the control system 100 can issue instructions and data, shown as commands 85, which programmatically controls various electromechanical interfaces of the vehicle 10. The commands 85 can serve to control operational aspects of the vehicle 10, including propulsion, braking, steering, and auxiliary behavior (e.g., turning lights on). In examples described herein, the commands 85 can further serve to control output devices of a sensory stimulation system, such as visual, audio, haptic/tactile, and/or airflow output devices to provide sensory stimulation to passengers of the AV 10.

The AV 10 can be equipped with multiple types of sensors 101, 103, 105, which combine to provide a computerized perception of the space and environment surrounding the vehicle 10. Likewise, the control system 100 can operate within the AV 10 to receive sensor data from the collection of sensors 101, 103, 105, and to control various electromechanical interfaces for operating the vehicle on roadways.

In more detail, the sensors 101, 103, 105 operate to collectively obtain a complete sensor view of the vehicle 10, and further to obtain situational information proximate to the vehicle 10, including any potential hazards proximate to the vehicle 10. By way of example, the sensors 101, 103, 105 can include multiple sets of cameras sensors 101 (video camera, stereoscopic pairs of cameras or depth perception cameras, long range cameras), remote detection sensors 103 such as provided by radar or LIDAR, proximity or touch sensors 105, and/or sonar sensors (not shown).

Each of the sensors 101, 103, 105 can communicate with the control system 100 utilizing a corresponding sensor interface 110, 112, 114. Each of the sensor interfaces 110, 112, 114 can include, for example, hardware and/or other logical component which is coupled or otherwise provided with the respective sensor. For example, the sensors 101, 103, 105 can include a video camera and/or stereoscopic camera set which continually generates image data of an environment of the vehicle 10. As an addition or alternative, the sensor interfaces 110, 112, 114 can include a dedicated processing resource, such as provided with a field programmable gate array ("FPGA") which can, for example, receive and/or process raw image data from the camera sensor.

In some examples, the sensor interfaces 110, 112, 114 can include logic, such as provided with hardware and/or programming, to process sensor data 99 from a respective sensor 101, 103, 105. The processed sensor data 99 can be outputted as sensor data 111. As an addition or variation, the control system 100 can also include logic for processing raw or pre-processed sensor data 99.

According to one implementation, the vehicle interface subsystem 90 can include or control multiple interfaces to control mechanisms of the vehicle 10. The vehicle interface subsystem 90 can include a propulsion interface 92 to electrically (or through programming) control a propulsion component (e.g., an accelerator pedal), a steering interface 94 for a steering mechanism, a braking interface 96 for a braking component, and a lighting/auxiliary interface 98 for exterior lights of the vehicle. According to implementations described herein, control signals 119 can be transmitted to a stimulation interface 95 of the vehicle interface subsystem 90 to control sensory stimulation outputs through various output devices of a sensory stimulation system of the AV 10. The vehicle interface subsystem 90 and/or the control system 100 can further include one or more controllers 84 which can receive commands 85 from the control system 100. The commands 85 can include route information 87 and operational parameters 89—which specify an operational state of the vehicle 10 (e.g., desired speed and pose, acceleration, etc.)—as well as stimulation commands 85 to control the output devices of the sensory stimulation system.

The controller(s) 84 can generate control signals 119 in response to receiving the commands 85 for one or more of the vehicle interfaces 92, 94, 95, 96, 98. The controllers 84 can use the commands 85 as input to control propulsion, steering, braking, and/or other vehicle behavior while the AV 10 follows a current route. Thus, while the vehicle 10 actively drives along the current route, the controller(s) 84 can continuously adjust and alter the movement of the vehicle 10 in response to receiving a corresponding set of commands 85 from the control system 100. Absent events or conditions which affect the confidence of the vehicle 10 in safely progressing along the route, the control system 100 can generate additional commands 85 from which the controller(s) 84 can generate various vehicle control signals 119 for the different interfaces of the vehicle interface subsystem 90.

According to examples, the commands 85 can specify actions to be performed by the vehicle 10. The actions can correlate to one or multiple vehicle control mechanisms (e.g., steering mechanism, brakes, etc.). The commands 85 can specify the actions, along with attributes such as magnitude, duration, directionality, or other operational characteristics of the vehicle 10. By way of example, the commands 85 generated from the control system 100 can specify a relative location of a road segment which the AV 10 is to occupy while in motion (e.g., change lanes, move into a center divider or towards shoulder, turn vehicle, etc.). As other examples, the commands 85 can specify a speed, a change in acceleration (or deceleration) from braking or accelerating, a turning action, or a state change of exterior lighting or other components. The controllers 84 can translate the commands 85 into control signals 119 for a corresponding interface of the vehicle interface subsystem 90. The control signals 119 can take the form of electrical signals which correlate to the specified vehicle action by virtue of electrical characteristics that have attributes for magnitude, duration, frequency or pulse, or other electrical characteristics.

In an example of FIG. 1, the control system 100 can include a route planner 122, stimulation logic 121, event logic 124, and a vehicle control 128. The vehicle control 128 represents logic that converts alerts of event logic 124 ("event alert 135") and sensory outputs 133 by the stimulation logic 121 into commands 85 that specify a set of vehicle actions and/or sensory stimulation outputs.

Additionally, the route planner 122 can select one or more route segments that collectively form a path of travel for the AV 10 when the vehicle 10 is on a current trip (e.g., servicing a pick-up request). In one implementation, the route planner 122 can specify route segments 131 of a planned vehicle path which defines turn by turn directions for the vehicle 10 at any given time during the trip. The route planner 122 may utilize the sensor interface 110 to receive GPS information as sensor data 111. The vehicle control 128 can process route updates from the route planner 122 as commands 85 to progress along a path or route using default driving rules and actions (e.g., moderate steering and speed).

According to examples described herein, the control system 100 can further execute stimulation logic 121 to provide sensory outputs 133 to the vehicle control 128 based on maneuvers performed by the AV 10. In some aspects, the stimulation logic 121 can utilize route information (e.g., indicating a granular path to be traveled by the AV 10), situational data (e.g., indicating the surrounding entities, road signs, traffic signals, etc. proximate to the AV 10), and/or action information indicating the planned actions to be performed by the control system 100 in maneuvering the AV 10. Based on the foregoing collective data, the stimulation logic 121 can generate sensory outputs 133 corresponding to sensory stimulations to be provided to riders of the AV 10 based on anticipated or current maneuvers of the AV 10. Such maneuvers can include acceleration, braking, and directional change maneuvers with relatively fine granularity. For example, the maneuvers can include minor swerves, light braking and acceleration, and low speed turns as well as harder braking and acceleration and normal to aggressive turns. Additionally or alternatively, the stimulation logic 121 can utilize sensor data 111 indicating acceleration or inertial information (e.g., specific force or angular rate) in order to generate the sensory outputs 133.

The sensory outputs 133 can be processed by the vehicle control 128 to generate stimulation commands 85, which the controller 84 can process to operate interior cabin stimulation systems of the AV 10. For example, based on the sensory commands 85, the controller 84 can generate control signals 119 to engage the interior visual, audio, haptic/tactile, airflow, and seat positioning systems via the stimulation interface 95 in order to provide the rider(s) with sensory stimulation to substantially correlate vestibular perception with visual perception. Such stimulation outputs can provide sufficient correlation or agreement between the vestibular sense of movement and visual perception to prevent kinetosis and its unpleasant symptoms. Detailed description of the sensory stimulation system is provided below with respect to FIGS. 2 through 5B.

In certain implementations, the event logic 124 can trigger a response to a detected event. A detected event can correspond to a roadway condition or obstacle which, when detected, poses a potential hazard or threat of collision to the vehicle 10. By way of example, a detected event can include an object in the road segment, heavy traffic ahead, and/or wetness or other environmental conditions on the road segment. The event logic 124 can use sensor data 111 from cameras, LIDAR, radar, sonar, or various other image or sensor component sets in order to detect the presence of such events as described. For example, the event logic 124 can detect potholes, debris, objects projected to be on a collision trajectory, and the like. Thus, the event logic 124 can detect events which enable the control system 100 to make evasive actions or plan for any potential threats.

When events are detected, the event logic 124 can signal an event alert 135 that classifies the event and indicates the type of avoidance action to be performed. Additionally, the control system 100 can determine whether an event corresponds to a potential incident with a human driven vehicle, a pedestrian, or other human entity external to the AV 10. In turn, the vehicle control 128 can determine a response based on the score or classification. Such response can correspond to an event avoidance action 145, or an action that the vehicle 10 can perform to maneuver the vehicle 10 based on the detected event and its score or classification. By way of example, the vehicle response can include a slight or sharp vehicle maneuvering for avoidance using a steering control mechanism and/or braking component. The event avoidance action 145 can be signaled through the commands 85 for controllers 84 of the vehicle interface subsystem 90.

When an anticipated dynamic object of a particular class does in fact move into position of likely collision or interference, some examples provide that event logic 124 can signal the event alert 135 to cause the vehicle control 128 to generate commands 85 that correspond to an event avoidance action 145. For example, in the event of a bicycle crash in which the bicycle (or bicyclist) falls into the path of the vehicle 10, event logic 124 can signal the event alert 135 to avoid the collision. The event alert 135 can indicate (i) a classification of the event (e.g., "serious" and/or "immediate"), (ii) information about the event, such as the type of object that generated the event alert 135, and/or information indicating a type of action the vehicle 10 should take (e.g., location of object relative to path of vehicle, size or type of object, etc.). In addition, the stimulation logic 121 can utilize the event alert 135 to cause the controller 84 to generate a corresponding output via the stimulation interface 95 to provide the rider with sensory stimulation to anticipate or react to the event.

Figure 2:
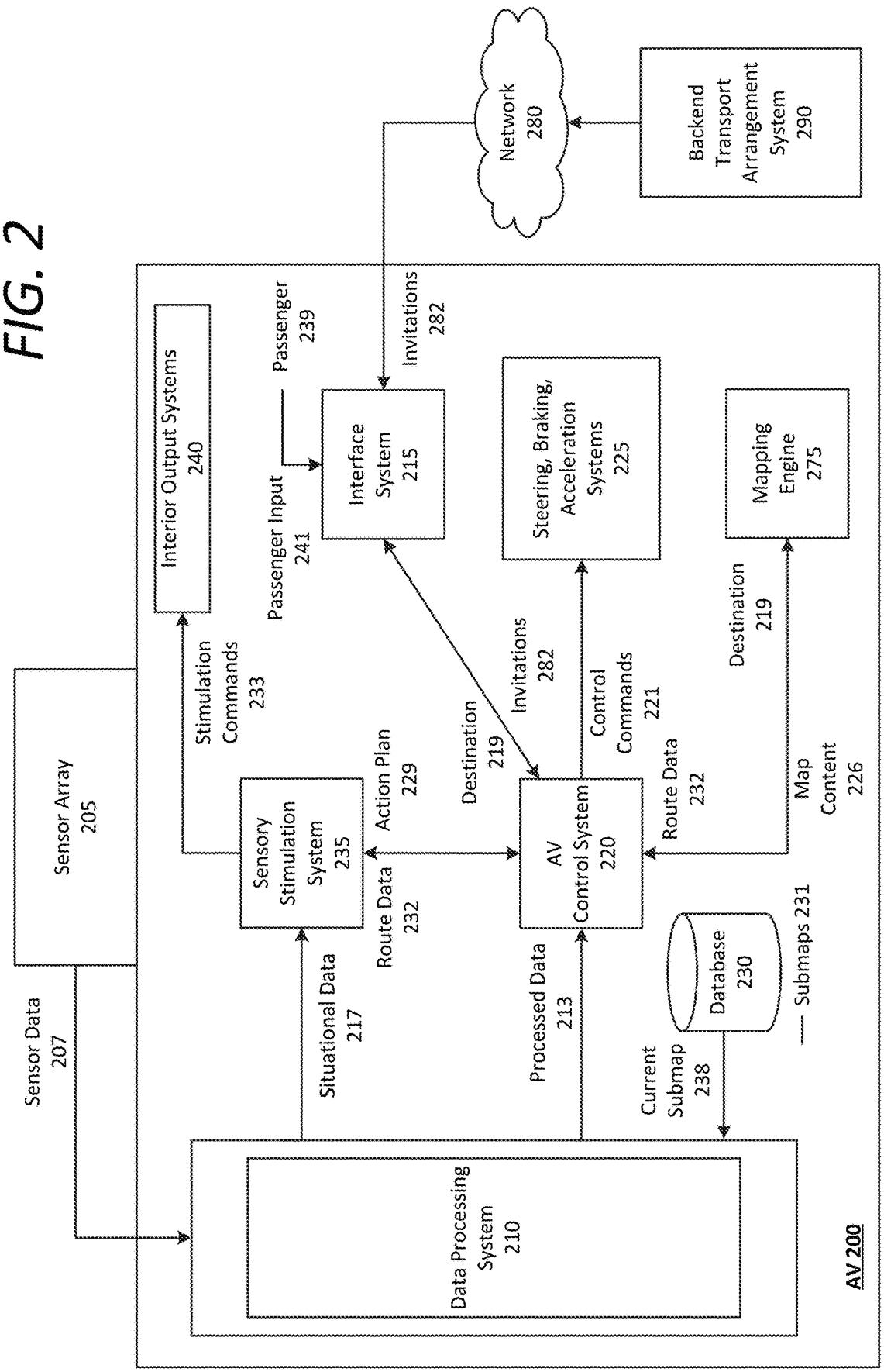
FIG. 2 is a block diagram illustrating an example autonomous vehicle including a sensory stimulation system, as described herein.

FIG. 2 is a block diagram illustrating an example AV 200 including a sensory stimulation system 235, as described herein. The AV 200 shown in FIG. 2 can include some or all aspects and functionality of the AV 10 described with respect to FIG. 1. Referring to FIG. 2, the AV 200 can include a sensor array 205 that can provide sensor data 207 to an on-board data processing system 210. As described herein, the sensor array 205 can include any number of active or passive sensors that continuously detect a situational environment of the AV 200. For example, the sensor array 205 can include a number of camera sensors (e.g., stereoscopic cameras), LIDAR sensor(s), proximity sensors, radar, and the like. The data processing system 210 can utilize the sensor data 207 to detect the situational conditions of the AV 200 as the AV 200 travels along a current route. For example, the data processing system 210 can identify potential obstacles or road hazards—such as pedestrians, bicyclists, objects on the road, road cones, road signs, animals, etc.—in order to enable an AV control system 220 to react accordingly.

In certain implementations, the data processing system 210 can utilize sub-maps 231 stored in a database 230 of the AV 200 (or accessed remotely from the backend system 290 via the network 280) in order to perform localization and pose operations to determine a current location and orientation of the AV 200 in relation to a given region (e.g., a city).

The data sub-maps 231 in the database 230 can comprise previously recorded sensor data, such as stereo camera data, radar maps, and/or point cloud LIDAR maps. The sub-maps 231 can enable the data processing system 210 to compare the sensor data 207 from the sensor array 205 with a current sub-map 238 to identify obstacles and potential road hazards in real time. The data processing system 210 can provide the processed sensor data 213—identifying such obstacles and road hazards—to the AV control system 220, which can react accordingly by operating the steering, braking, and acceleration systems 225 of the AV 200 to perform low level maneuvering.

In many implementations, the AV control system 220 can receive a destination 219 from, for example, an interface system 215 of the AV 200. The interface system 215 can include any number of touch-screens, voice sensors, mapping resources, etc., that enable a passenger 239 to provide a passenger input 241 indicating the destination 219. For example, the passenger 239 can type the destination 219 into a mapping engine 275 of the AV 200, or can speak the destination 219 into the interface system 215. Additionally or alternatively, the interface system 215 can include a wireless communication module that can connect the AV 200 to a network 280 to communicate with a backend transport arrangement system 290 to receive invitations 282 to service a pick-up or drop-off request. Such invitations 282 can include the destination 219 (e.g., a pick-up location), and can be received by the AV 200 as a communication over the network 280 from the backend transport arrangement system 290. In many aspects, the backend transport arrangement system 290 can manage routes and/or facilitate transportation for users using a fleet of autonomous vehicles throughout a given region. The backend transport arrangement system 290 can be operative to facilitate passenger pick-ups and drop-offs to generally service pick-up requests, facilitate delivery such as packages or food, and the like.

Based on the destination 219 (e.g., a pick-up location), the AV control system 220 can utilize the mapping engine 275 to receive route data 232 indicating a route to the destination 219. In variations, the mapping engine 275 can also generate map content 226 dynamically indicating the route traveled to the destination 219. The route data 232 and/or map content 226 can be utilized by the AV control system 220 to maneuver the AV 200 to the destination 219 along the selected route. For example, the AV control system 220 can dynamically generate control commands 221 for the autonomous vehicle's steering, braking, and acceleration systems 225 to actively drive the AV 200 to the destination 219 along the selected route.

In many examples, while the AV control system 220 operates the steering, braking, and acceleration systems 225 along the current route on a high level, the processed data 213 provided to the AV control system 220 can indicate low level occurrences, such as obstacles and potential hazards, to which the AV control system 220 can make decisions and react. For example, the processed data 213 can indicate a pedestrian crossing the road, traffic signals, stop signs, other vehicles, road conditions, traffic conditions, bicycle lanes, crosswalks, pedestrian activity (e.g., a crowded adjacent sidewalk), and the like. The AV control system 220 can respond to the processed data 213 by generating control commands 221 to reactively operate the steering, braking, and acceleration systems 225 accordingly.

According to examples described herein, the AV 200 can include a sensory stimulation system 235 that can operate a number of interior output systems 240 based on motion actions or maneuvers of the AV 200. The sensory stimulation system 235 can provide such stimulation outputs reactively in response to AV maneuvers, or preemptively in anticipation of such maneuvers. In many examples, the sensory stimulation system 235 in combination with the interior output systems 240 can provide a subconscious or unconscious learning environment for correlating vestibular sensing with visual perception in order to prevent motion sickness or unexpected surprises when the AV 200 performs ordinary or emergency maneuvers.

In many examples, the sensory stimulation system 235 can dynamically receive an action plan 229 from the AV control system 220 indicating the immediate maneuvers to be performed by the AV control system 220. For example, the action plan 229 can correspond to the control commands 221 that the AV control system 220 generates to operate the steering, braking, and acceleration systems 225 of the AV 200. Thus, the action plan 229 can indicate low level inputs to be provided to, for example, an accelerator, brake, or steering mechanism of the AV 200 as the AV 200 is autonomously operated along a current route. The sensory stimulation system 235 can process the action plan 229 to generate stimulation commands 233 for the interior output systems 240—such as visual stimulation, dynamic seat adjustments (e.g., adjusting pitch, roll, and/or yaw), haptic stimulation, and/or air pressure stimulation.

Additionally or alternatively, the sensory stimulation system 235 can receive situational data 217 from the on-board data processing system 210. The situational data 217 can include data identifying external entities and their locations proximate to the AV 200. External entities can include any proximate pedestrians, bicyclists, human-driven vehicles, or any other human within proximity of the AV 200. According to an example implementation, the interior output systems 240 can include one or more displays, such as a large dash display above a center console area of the AV 200, or multiple dash displays prominently visible by each of the passengers. The sensory stimulation system 235 can dynamically generate a live map view of the immediate environment of the AV 200 for presentation on the displays. For example, the sensory stimulation system 235 can continuously present a three-quarter perspective or pseudo-three-dimensional perspective view from above and behind the AV 200, and dynamically generate virtual representations of the AV 200 as well as each of the proximate external entities identified in the situational data 217. Thus, as the AV 200 travels, the displayed presentation can be dynamically updated to show a live view of the AV 200 itself traveling along a current route and representations of external entities identified by the sensory stimulation system 235 in the situational data 217.

In some aspects, the sensory stimulation system 235 can present actual live video and/or LIDAR data on the display(s) that indicate an entire situational environment of the AV 200 (e.g., in a forward operational field of view of the AV 200). In such aspects, the sensory stimulation system 235 can generate augmented reality content to superimpose certain features in the live presentation, and/or present augmented reality indicators that provide information regarding the route to be traveled by the AV 200 and low level maneuvers to be performed by the AV 200, as described herein.

In variations, the sensory stimulation system 235 can further receive route data 232 indicating the current route traveled by the AV 200 to the destination 219. On a coarse granular level, the sensory stimulation system 235 can generate route indicators on the presented live map based on the route data 232, where the route indicators can highlight the current route traveled by the AV 200. On a finer granular level, the sensory stimulation system 235 can utilize the action plan 229 from the AV control system 220—as well as the route data 232 and situational data 217—to generate low level indications of the AV 200 immediate actions for the presented display. For example, the action plan 229 can identify subtle actions to be performed by the AV control system 220, such as individual lane changes, yielding actions, planned braking and acceleration actions, avoidance maneuvers, and even emergency maneuvers. The sensory stimulation system 235 can utilize this low level action plan 229 data to generate preemptive indicators on the dynamically displayed presentation of each of the AV's 200 maneuvers. Such low level indicators can include generated symbols and/or arrows on the live map view (e.g., color coded arrows to indicate acceleration, braking, and turning actions), audio speech preemptively describing the actions or maneuvers, audio sounds indicating each maneuver (e.g., jingles or tones for each respective action), or displayed words describing the actions.

Utilizing each of the situational data 217, the route data 232, and the action plan 229 from the AV control system 235, the sensory stimulation system 235 can dynamically generate stimulation commands 233 to continuously stream the live presentation via the display(s) of the interior output systems 240. The live presentation can preemptively provide the passenger(s) with each low level maneuver to be performed by the AV control system 220, as well as a route plan from the route data 232 and representations of proximate external entities from the situational data 217. Utilizing the actual control data of the AV control system 220, the live presentation can provide far more granular detail of the AV's 200 route and actions than currently available live views, which typically provide only a cursory route plan. Furthermore, the sensory stimulation system 235 can provide the live presentation as a standalone visual stimulation for the passenger(s), or in conjunction with other sensory stimulations utilizing various output devices of the interior output systems 240.

In addition or as an alternative to the above live presentation, the sensory stimulation system 235 can further utilize the action plan data 229 to generate stimulation commands 233 for a fixed lighting system of the interior output systems 240. In some examples, the fixed lighting system can comprise a light bar that includes a string of lighting elements (e.g., RGB LEDS) circumscribing the interior of the AV 200. For example, the light bar can circumscribe an edge of the ceiling of the AV 200. Additionally or alternatively, the light bar can circumscribe a mid-plane of the AV interior (e.g., just below the windows). According to one example, the interior output systems 240 can include multiple light bars or lighting elements fixed within the interior of the AV 200. The sensory stimulation system 235 can utilize the action plan 229 to generate stimulation commands 233 that cause the lighting system to output visual sensory indications of the AV's 200 upcoming and/or current maneuvers.

For example, the sensory stimulation system 235 can generate stimulation commands 233 controlling lighting outputs that indicate each acceleration, braking, and directional change maneuver to be performed by the AV control system 220. The stimulation commands 233 can trigger certain portions of the lighting system (e.g., illuminating the left side of a light bar to indicate an upcoming or current left turning maneuver), control color and brightness or a blink rate (e.g., to indicate acceleration versus braking, and the intensities of such maneuvers and actions). In certain aspects, the sensory stimulation system 235 can provide lighting outputs to coincide with the acceleration, braking, and steering systems 225, such that the vestibular and visual perception of passengers may be readily trained to anticipate or otherwise react to each maneuver, however minor.

As an example, acceleration may be correlated with green, braking with red, and turning with yellow. As the AV 200 travels, the sensory stimulation system 235 can generate stimulation commands 233 that cause the lighting system of the interior output systems 240 to preemptively and/or conjunctively illuminate the lighting system to indicate acceleration, braking, and turning. Furthermore, the sensory stimulation system 235 can control brightness to indicate an intensity or strength of each acceleration, braking, and turning maneuver, as well as illuminating select portions of the lighting system to indicate directional aspects of the maneuvering. The sensory stimulation system 235 can generate such stimulation commands 233 dynamically to provide passengers with visual indications or feedback of the AV's 200 movements.

Additionally or alternatively, the sensory stimulation system 235 can utilize the action plan data 229, as well as the situational data 217 and route data 232 to provide further stimulation to riders, such as haptic or tactile stimulation, air pressure stimulation, and/or rotating the seats on principal axes to provide perceived force to the passenger(s). Examples and detailed explanation of such stimulations by the sensory stimulation system 235 is provided in the below description of FIG. 3.

Figure 3:
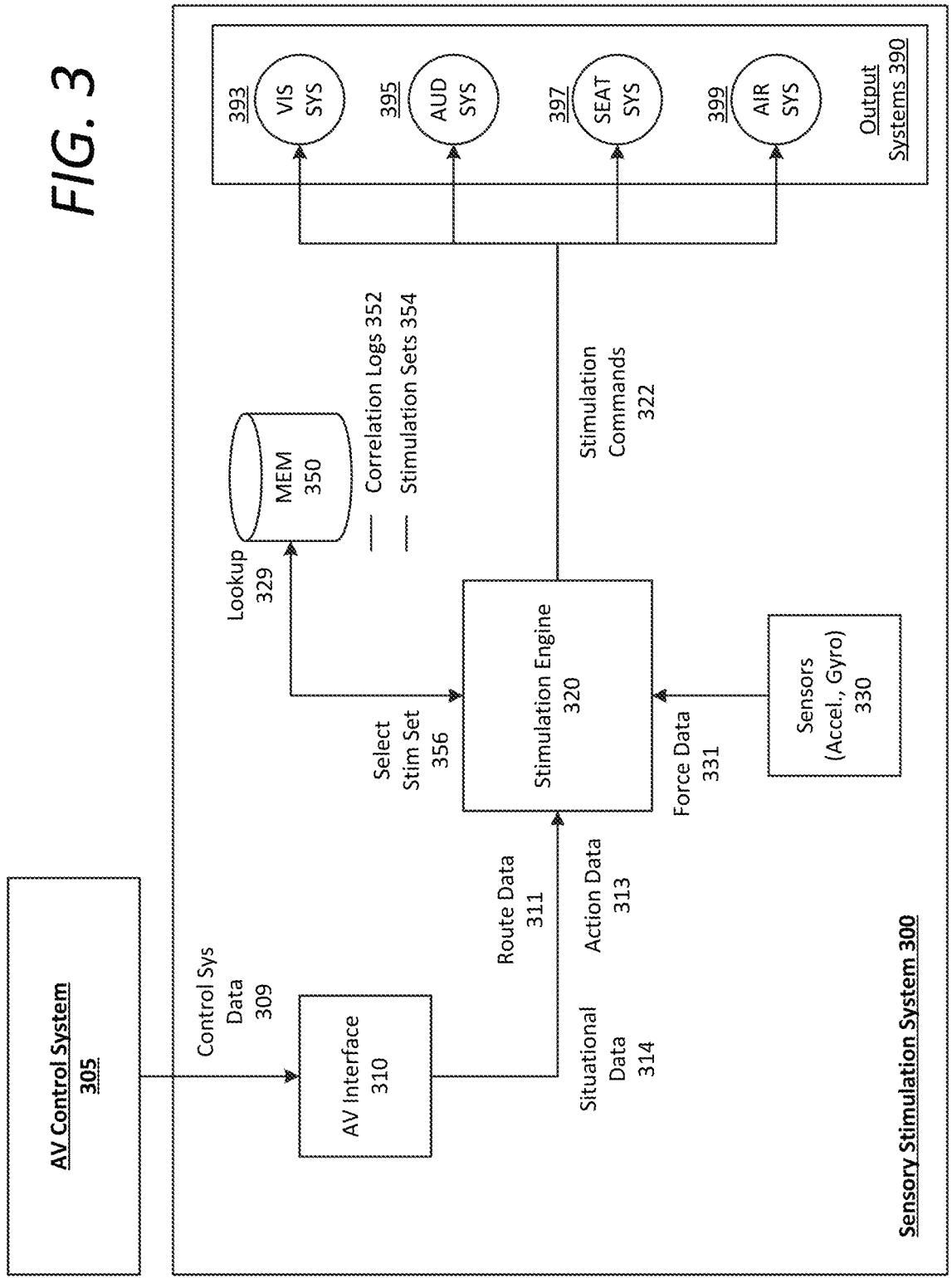
FIG. 3 is a block diagram illustrating an example sensory stimulation system, as shown and described herein.

FIG. 3 is a block diagram illustrating an example sensory stimulation system 300 as shown and described herein. The sensory stimulation system 300 shown and described with respect to FIG. 3 can include some or all of the functionality of the sensory stimulation system 235 and the interior output systems 240 discussed above with respect to FIG. 2. Referring to FIG. 3, the sensory stimulation system 300 can include a memory 350 that stores correlation logs 352 providing correlations between motion actions and maneuvers of the AV 200 with stimulation sets 354 that can be executed to provide riders with sensory stimulation via the output systems 390. Furthermore, the sensory stimulation system 300 can include a stimulation engine 320 that can process situational data 314, route data 311, and/or action data 313 provided from the AV control system 305.

The sensory stimulation system 300 can include an AV interface 310 to receive control system data 309 from the AV control system 305. In some aspects, the control system data 309 can include the action data 313 indicating the immediate actions or maneuvers to be executed by the AV control system 305. Additionally, the control system data 309 can include situational data 314 and/or route data 311, as described above. The control system data 309 can be processed by a stimulation engine 320 of the sensory stimulation system 300. Based on the control system data 309, the stimulation engine 320 can determine a number of sensory stimulation outputs to generate via the output systems 390.

As described herein, the output systems 390 of the sensory stimulation system 300 can include a visual system 393 that can comprise the display(s) and/or lighting system (e.g., light bar(s) circumscribing the interior of the AV). Utilizing the control system data 309 (e.g., the situational data 314, route data 311, and/or action data 313), the stimulation engine 320 can generate stimulation commands 322 to provide a live presentation of the AV, described above, and/or lighting outputs that indicate each of the maneuvers of the AV, also described above, using the visual system 393.

In addition or as an alternative to the foregoing aspects, the sensory stimulation system 300 can utilize the control system data 309 to generate stimulation commands 322 for other output systems 390, such as the audio system 395, a seat response system 397, and/or an airflow system 399. The audio system 395 can be implemented with the AV's manufacturer installed speaker sets or as an independent speaker set. In some aspects, the audio system 395 can be utilized in conjunction with other output devices of the sensory stimulation system 300 to indicate instant maneuvers to be performed by the AV (e.g., via output jingles, directional tones, or speech).

The seat response system 397 can include haptic seat technology that can provide vibrational or other tactile feedback to the passenger via the seats. For example, haptic seats can provide vibrational pulses to the whole seat, or select portions of the seat based on the maneuver (e.g., left side or right side to indicate turns, upper portion to indicate acceleration, and forward seat cushion to indicate braking). Furthermore, the sensory stimulation system 300 can vary an intensity or strength of the haptic feedback and/or vibrational pulses based on an intensity or strength of the maneuver.

In certain aspects, the seat response system 397 can include a number of motors and a pivoting mechanism for each seat to enable the stimulation engine 320 to adjust a pitch, roll, and/or yaw of each seat in response to the control system data 309. For example, the action data 313 from the AV control system 305 can indicate an upcoming sharp left turn (e.g., to be performed within one or two seconds). In response, the stimulation engine 320 can generate a stimulation command 322 to roll the seats to the left to direct the force felt by the rider downward (into the seat cushion) as opposed to laterally based on the centripetal force of the AV as it makes the turn. For acceleration and braking, the stimulate engine 320 can generate stimulation commands 322 causing the seats to pitch forward or backward. In some aspects, the stimulation engine 320 can further control the yaw of the seats, for example, when the AV performs turning maneuvers or combinations of turning and acceleration or braking. Additionally or alternatively, based on the action data 313, the stimulation engine 320 can generate combinations of pitch, roll, and yaw stimulation commands 322 for the seat response system 397 dynamically as the AV travels along a current route.

The airflow system 399 can output directional airstreams to provide riders with stimulation indicating movement of the AV. As provided herein, the airflow system 399 can utilize the air conditioning system of the AV, or can be provided as a customized system capable of providing directional airstreams to the rider(s). The stimulation engine 320 can operate compressed air valves and/or fans that can generate air pulses or wind that can indicate a direction of travel, speed, acceleration, braking, and changes in direction. The airflow system 399 can include various outlets to provide the airstreams from multiple directions. For example, the airflow system 399 can include air ducting and outlets through the dash (or utilize existing ducts of the AV), through the doors, the ceiling, and/or the seats of the AV. As an example, the airflow system 399 can include outlets on the headrests of the passenger seats to provide airstream outputs or an air pulse when the AV performs a specified action (e.g., performs an avoidance maneuver). As another example, the stimulation engine 320 can cause the airflow system 399 to provide simulated wind to provide the riders with airflow stimulation indicating that the AV is in motion.

The stimulation engine 320 can control various parameters of the airflow system 399 based on the action data 313, such as airflow speed/intensity, direction (e.g., 360° around the riders both radially and azimuthally), temperature, timing, pulse rate, and height (e.g., aiming at the rider's head, shoulders, torso, arms, legs, feet, etc.). In many aspects, the stimulation engine 320 can generate stimulation commands 322 to utilize the airflow system 399 individually, or in conjunction with the other output devices 390 of the sensory stimulation system 300.

Additionally, each of the output systems 390 may be activated or deactivated by the rider. Accordingly, if the rider wishes to deactivate, for example, the seat response system 397, the rider can provide input to do so. For example, the display(s) of the visual system 393 can include a user interface to enable the rider to access a menu indicating the various stimulation outputs of the sensory stimulation system 300. The rider may activate or deactivate any one or all of the output systems 390 as desired. In certain examples, the rider can control a sensitivity of the output systems 390 to increase or decrease stimulation responses. For example, a rider may wish to disable the audio system 395 of the sensory stimulation system 300 in order to listen to music or the radio. As another example, the rider may wish to disable the live presentation to view a news or entertainment program. Accordingly, the rider may adjust or disable any one or more of the output systems 390 to his or her liking.

According to examples described herein, the AV interface 310 can receive control system data 309 from the AV control system 305, and parse the data into various aspects, such as situational data 314 indicating the situational environment and external entities, route data 311 indicating a current route traveled by the AV to a destination, and action data 313 corresponding to immediate actions to be executed by the AV control system 305 in autonomously operating the AV's acceleration, braking, and steering systems. In certain examples, the sensory stimulation system 300 can further include sensors 330, such as one or more accelerometers and/or gyroscopic sensors to provide force data 331 to the stimulation engine 320 to reactively generate stimulation commands 322.

In one aspect, the stimulation engine 320 can utilize the situational data 314 and the route data 311 to provide a live, visual presentation on displays of the visual system 393. The stimulation engine 320 can further utilize the action data 313 from the control system 305 to dynamically generate action indicators—comprising symbols, arrows, colors, words, etc.—that indicate the actions and maneuvers being performed or to be performed by the AV. Thus, the displayed live presentation can include low level granular information indicating each particular action the AV control system 305 performs when autonomously operating the AV's acceleration, braking, and steering systems.

Additionally or alternatively, based on the action data 313, the stimulation engine 320 can perform lookups 329 in the correlation logs 352 of the memory 350 to identify a selected stimulation set 356 that matches the maneuver(s) or action(s) to be performed. For example, the action data 313 can indicate that the AV control system 305 is operating the AV at freeway speeds and will exit the freeway with relatively hard braking to make a tight right turn. A stimulation set 354 for such a combination can be selected and utilized by the stimulation engine 320 to generate a set of stimulation commands 322 for each of the visual 393, audio 395, seat response 397, and airflow systems 399 to provide stimulation to the rider(s) to anticipate the maneuver and compensate for the experienced forces caused by the maneuver. For example, the stimulation commands 322 can cause the lighting elements (e.g., a light bar) of the visual system 393 to flash red to indicate the hard braking, and then provide bright yellow outputs on a right-hand portion of the light bar to indicate the hard right turn.

Additionally or as an alternative, the stimulation commands 322 can generate an audio output via the audio device 395 to provide a speech output or tonal audio stimulations to indicate each step of the maneuver. Additionally or alternatively still, the stimulation commands 322 can cause the seat response system 397 to pitch the seat rearwards to compensate for the forward braking forward, and then roll the seats rightward to compensate for the turning force as the AV makes the sharp right-hand turn. As a further addition or alternative, as the AV travels at freeway speeds, the stimulation commands 322 can cause the airflow system 399 to provide a gentle and continuous rearward breeze, and provide a directional pulse of air as the AV goes under braking (e.g., from the rear of the rider), and another directional pulse as the AV turns right (e.g., from the front right side of the rider's head).

Such sensory stimulations using the output systems 390 can be generated primarily based on the action data 313 received from the AV control system 305, which can include preemptive maneuvering information as well as currently executing maneuver information. Thus, certain sensory stimulations can be provided prior to the maneuvers being executed (e.g., the airflow stimulations, visual stimulations using the light bar, and haptic seat stimulations), and other sensory stimulations can be provided as the maneuver is being performed (e.g., the seat roll and pitch response stimulations).

In variations, the force data 331 provided by the sensors 330 of the sensory stimulation system 300 can be utilized by the stimulation engine 320 to reactively operate one or more of the output systems 390. The force data 331 can indicate directional acceleration experienced by the AV due to the AV accelerating, braking, turning, experiencing bumps or other forces on a bumpy road, and combinations thereof (e.g., swerving or sliding). As an example, the seat roll, pitch, and yaw responses of the seat response system 397 can be based on the force data 331 generate by the sensors 330 of the sensory stimulation system 300. In other examples, the stimulation engine can generate stimulation commands 322 for the airflow system 399 and/or the visual system 393 based on the force data 331 from the sensors 330.

Thus, utilizing control system data 309 from the AV control system 305 and/or force data 331 from the sensors 330, the stimulation engine 320 can generate stimulation commands 322 that provide visual, audible, tactile/haptic, force (e.g., via pitching and rolling the seats), and/or airflow outputs to provide vestibular stimulation to the rider(s) to prevent or mitigate the effects of kinetosis. Each of the output systems 390 can be variably controlled by the stimulation engine 320 based on an intensity of a particular maneuver or motion action. Furthermore, user input may be provided by a rider to activate, deactivate, or adjust the control parameters of any or all of the output systems 390.

Autonomous Vehicle in Operation

Figure 4:
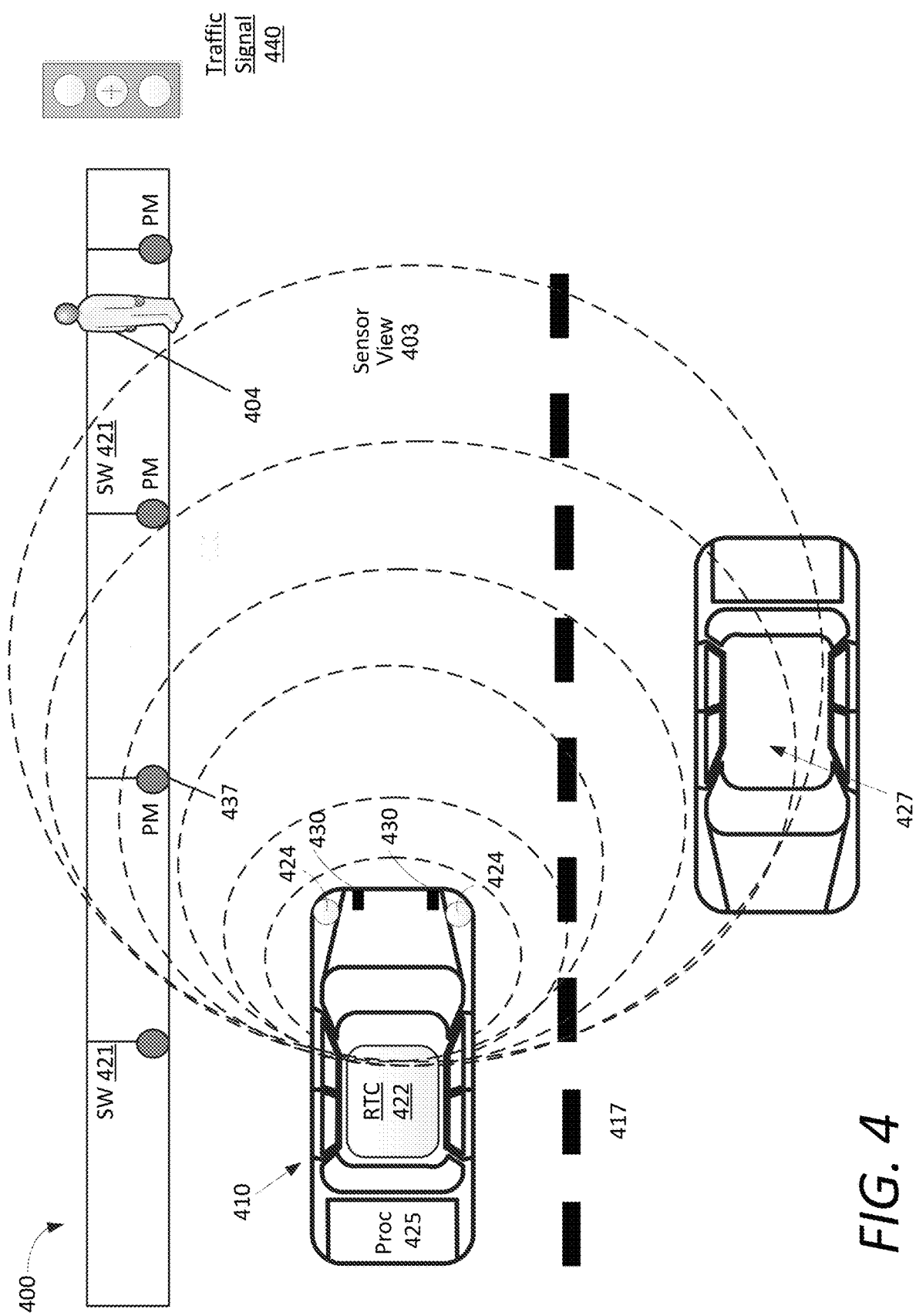
FIG. 4 shows an example of an autonomous vehicle utilizing sensor data to navigate an environment in accordance with example implementations.

FIG. 4 shows an example of an autonomous vehicle 410 utilizing sensor data to navigate an environment 400 in accordance with example implementations. In an example of FIG. 4, the autonomous vehicle 410 may include various sensors, such as a roof-top camera array (RTC) 422, front-facing cameras 424 and laser rangefinders 430. A data processing system 425, comprising a combination of one or more processors and memory units, can be positioned in a trunk of the vehicle 410.

According to an example, the vehicle 410 uses one or more sensor views 403 (e.g., a stereoscopic view or 3D LIDAR imaging of the environment 400) to scan a road segment on which the vehicle 410 traverses. The vehicle 410 can process image data, corresponding to the sensor views 403 from one or more sensors in order to detect objects that are, or may potentially be, in the path of the vehicle 410. In an example shown, the detected objects include a pedestrian 404 and another vehicle 427—each of which may potentially cross into a road segment 415 along which the vehicle 410 traverses. The vehicle 410 can use information about the road segment and/or image data from the sensor views 403 to determine that the road segment includes a divider 417 and an opposite lane, a traffic signal 440, and a sidewalk (SW) 421 and sidewalk structures such as parking meters (PM) 437.

The vehicle 410 may determine the location, size, and/or distance of objects in the environment 400 based on the sensor view 403. For example, the sensor views 403 may be 3D sensor images that combine sensor data from the roof-top camera array 422, front-facing cameras 424, and/or laser rangefinders 430. Accordingly, the vehicle 410 may accurately detect the presence of objects in the environment 400, allowing the vehicle to safely navigate the route while avoiding collisions with other objects.

As described herein, a sensory stimulation system of the vehicle 410 can display a live presentation of external entities such as a bicyclist the pedestrian 404, and the human-driven vehicle 427 within the environment 400 through which the vehicle 410 travels. Furthermore, assuming that the vehicle 410 is operating at a steady speed, the vehicle 410 can utilize the sensor view 403 to identify that the traffic signal 440 has changed from a green state to a yellow state (as shown), which can cause the control system of the vehicle 410 to generate an action plan to apply the brakes of the vehicle 410 to decelerate the vehicle 410 at a certain rate (e.g., six meters per second per second) to come to a complete stop at the traffic signal 440. The sensory stimulation system of the vehicle 410 can utilize this action data to generate stimulation commands in order to provide stimulation outputs for the riders of the vehicle 410 and compensate or otherwise prepare the riders for the braking, as described herein.

According to examples, the vehicle 410 may further determine a probability that one or more objects in the environment 400 will interfere or collide with the vehicle 410 along the vehicle's current path or route. In some aspects, the vehicle 410 may selectively perform an avoidance action based on the probability of collision. The avoidance actions may include velocity adjustments, lane aversion, roadway aversion (e.g., change lanes or driver far from curb), light or horn actions, and other actions. In some aspects, the avoidance action may run counter to certain driving conventions and/or rules (e.g., allowing the vehicle 410 to drive across center line to create space with bicyclist).

For each such avoidance action, the sensory stimulation system can determine the planned maneuver and control the interior output systems (e.g., the visual, audio, seat response, haptic, and/or airflow systems) to provide sensory stimulation for the riders based on the maneuver. For example, a swerve maneuver can cause the sensory stimulation system to generate lighting, haptic, seat adjustment, and/or airflow responses to provide the riders with vestibular stimulation according to the maneuver, as provided herein. Such responses can provide at least some correlation between the riders' visual perception and the forces felt as the maneuvering is being performed.

Methodology

Figure 5A:
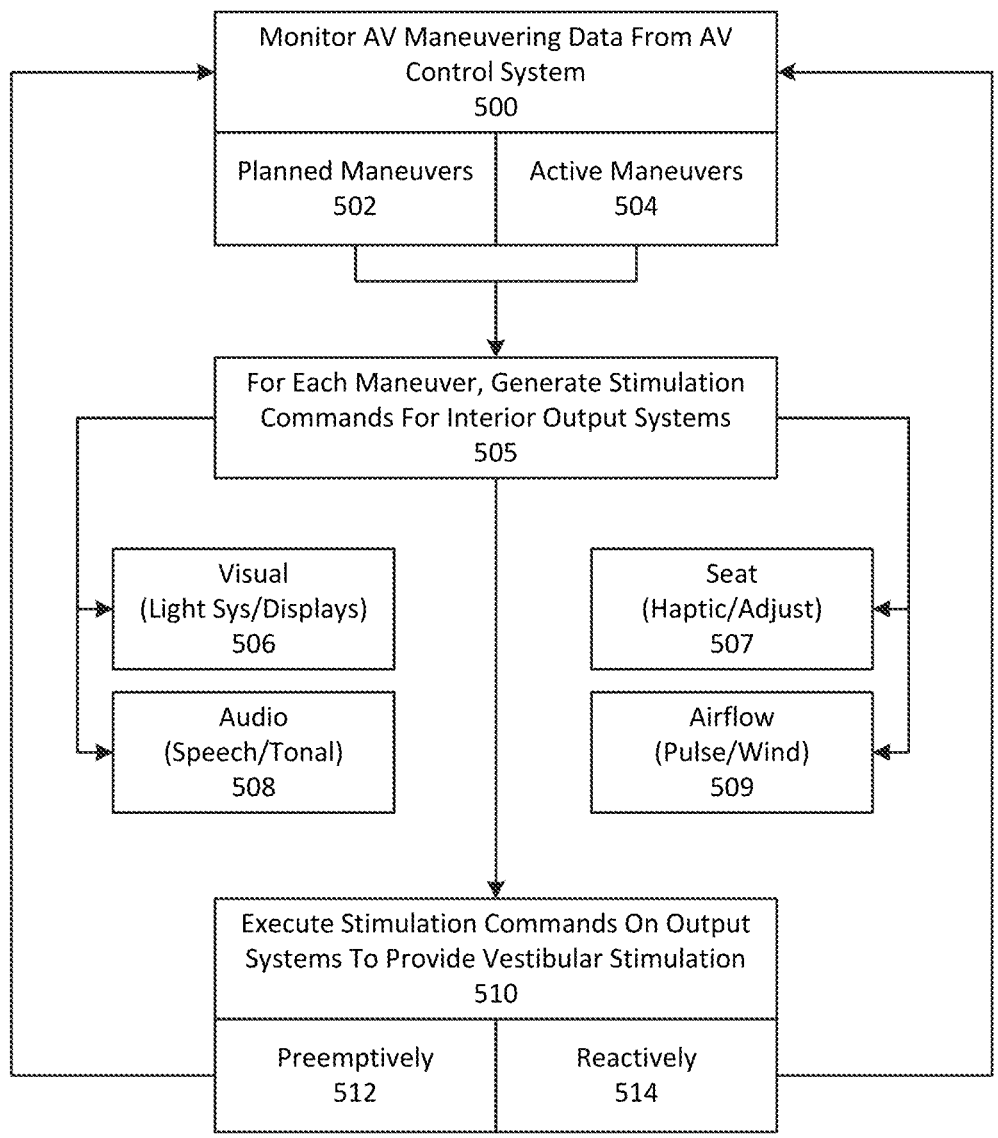
FIGS. 5A and 5B are flow charts describing example methods of operating a sensory stimulation system in accordance with example implementations.
Figure 5B:
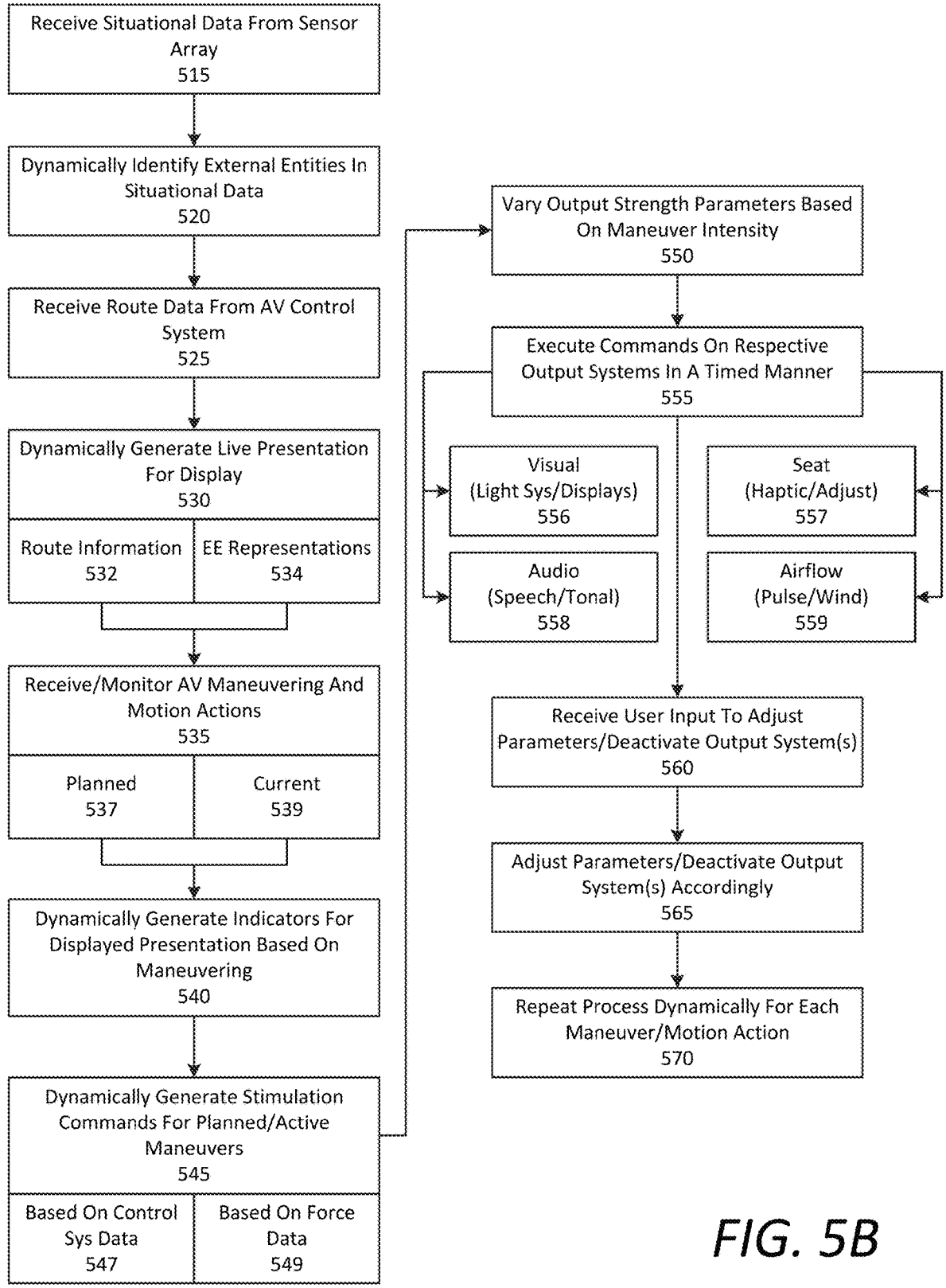

FIGS. 5A and 5B are flow charts describing example methods of operating a sensory stimulation system in accordance with example implementations. In the below descriptions of FIGS. 5A and 5B, reference may be made to like reference characters representing various features shown and described with respect to FIGS. 1 through 3. Furthermore, the methods described in connection with FIGS. 5A and 5B may be performed by example sensory stimulation systems 235, 300 shown and described with respect to FIGS. 2 and 3. Referring to FIG. 5A, the sensory stimulation system 300 can monitor AV maneuvering data from the AV control system 305 (500). In many examples, the AV maneuvering data can be included in action data 313 or an action plan 229 indicating planned, low level maneuvering to be performed by the AV control system 305 (502). Such low level planned maneuvering is distinguishable from a high level route plan indicating a current route in that monitoring the planned maneuvering (502) can provide the sensory stimulation system 300 with immediate actions by the AV control system 305 to be implemented in autonomously controlling the AV 200 (e.g., acceleration, steering, and braking actions). Additionally or alternatively, the sensory stimulation system 300 can monitor active maneuvers as they are being performed by the AV (504). For example, the sensory stimulation system 300 can receive the control commands 221 as they are being implemented, or monitor one or more sensors, such as an accelerometer and/or gyroscopic sensor indicating lateral force experienced by the AV 200.

For each maneuver, the sensory stimulation system 300 can generate stimulation commands 322 for the interior output systems 390 of the AV 200 (505). The stimulation commands 322 can be generated to compensate for anticipated lateral forces, provide sensory stimulation to "trick" or otherwise enable riders to correlate vestibular senses with visual perception, and prevent sensory disruptions that can affect rider comfort. The sensory stimulation system 300 can generate stimulation commands 322 for visual systems 393, such as the display(s) or lighting elements (e.g., a light bar) (506), seat response systems 397 to provide haptic feedback and/or pitch, roll, yaw sensations (507), an audio system 395 to provide speech and/or tonal stimulations indicating each maneuver (508), and/or an airflow system 399 to provide air pressure stimulation based on the maneuvers (509).

Accordingly, the sensory stimulation system 300 can dynamically execute the stimulation commands 322 on the output systems 390 to provide vestibular stimulation based on each of the maneuvers (510). Execution of the stimulation commands 322 can be performed preemptively (512) to enable riders to anticipate specific maneuvers (e.g., providing visual stimulation indicating upcoming braking), or reactively (514) as compensatory stimulation (e.g., rolling the seats during a turn, or providing simulated wind based on acceleration). As a dynamic process, the sensory stimulation system 300 can continuously function as the AV 200 is autonomously operated, the sensory stimulation system 500 can then continuously monitor AV maneuvering data accordingly (500).

Referring to FIG. 5B, the sensory stimulation system 300 can receive situational data 217 from the sensor array 205 of the AV 200 (515). The sensory stimulation system 300 can dynamically identify external entities in the situational data 217, such as bicyclists, pedestrians, other vehicles, and the like (520). The sensory stimulation system 300 can also receive route data 232 indicating a current route traveled by the AV 200 (525). Utilizing the situational data 217 and the route data 232, the sensory stimulation system 300 can generate a live presentation on a number of display devices (530). The live presentation can comprise a third-person highball view from above and behind the AV 200 and include a live map indicating route information (532) indicating the route traveled (e.g., a highlighted route on the live map), a virtual representation of the AV 200 as it travels along the route, and generated representations of the external entities superimposed on the live presentation and indicating their dynamic positions (534). Alternatively, the sensory stimulation system 300 can present live camera data and/or LIDAR data on the display(s), with one or more augmented reality elements generated thereon (e.g., highlighting the current route).

In many examples, the sensory stimulation system 300 can also receive and monitor AV maneuvering data from the AV control system 305 and other motion actions (e.g., road bumps, vertical movement on a windy road, etc.) (535). The sensory stimulation system 300 can identify planned maneuvers (e.g., to be executed within 5 seconds) (537) and current maneuvers being performed by the AV control system 305 (539). Based on the planned and/or current maneuvers of the AV control system 305, the sensory stimulation system 300 can dynamically generate live maneuvering indicators for the displayed live presentation (540). The sensory stimulation system 300 can input or otherwise superimpose the live maneuvering indicators, identifying planned as well as current maneuvers, onto the live presentation on top of the high level route information and live map. Such indicators can comprise color coded and/or flashing symbols, arrows, voice output, tonal outputs, etc., which can indicate granular, low level acceleration, turning, braking, swerving, lane changing, and other like actions.

Additionally or alternatively, the sensory stimulation system 300 can utilize the AV maneuvering data (e.g., action data 313) to dynamically generate stimulation commands 322 for each planned and/or active maneuver (545). The stimulation commands 322 can be based on maneuvering data received from the AV control system 305 (547), or based on force data 331 received from sensor(s) 330 of the sensory stimulation system 300 (549). In generating the stimulation commands 322, the sensory stimulation system 300 can vary output strength parameters based on maneuvering intensity (550). Such output strength parameters can include color, brightness, and/or blink rate for the live presentation and lighting elements, volume or audible urgency for the audio system 395, haptic strength, location, and pulse rate for the haptic system, angles and speed of pitch, roll, and/or yaw for the seat response system 397, and direction, pulse rate, wind speed, and/or temperature for the airflow system 399.

When the output strength parameters are configured and the stimulation commands 322 generated, the sensory stimulation system 300 can execute the commands on the respective output systems 390 in a timed manner (555). Specifically, the sensory stimulation system 300 can execute certain stimulation commands 322 using specified output systems 390 to preempt planned maneuvers, providing riders with anticipatory stimulation. Additionally or alternatively, the sensory stimulation system 300 can execute certain stimulation commands 322 using particular output systems 390 as maneuvers are being performed. For example, the sensory stimulation system 300 can execute visual stimulation commands 322 for a swerve maneuver 1-2 seconds prior to the AV control system 305 performing the maneuver (e.g., by generating a visual output indicating the swerve maneuver on a light bar). As the swerve maneuver is executed, the sensory stimulation system 300 can execute stimulation commands 322 that roll the seats into the turns. Thus, any combination of preemptive and reactive stimulation commands 322 can be executed to provide stimulation outputs through any combination of the output systems 390 for each respective maneuver performed by the AV 200. Such maneuvers can comprise any high or low level maneuver involving acceleration, braking, and turning the AV 200. As described herein, the stimulation commands 322 may be executed preemptively or reactively utilizing the visual system 393 (e.g., to provide light bar outputs or generate indicator on the display) (556), the seat response systems 397 to provide haptic feedback and/or pitch, roll, yaw sensations (557), the audio system 395 to provide speech and/or tonal stimulations indicating each maneuver (558), and/or the airflow system 399 to provide air pressure stimulation based on the maneuvers (559).

In certain aspects, the sensory stimulation system 300 can provide for user interactivity to enable a rider to control certain parameters of the output systems 390. For example, a rider may access a menu on a user interface of the display that can provide the adjustable parameters for each of the output systems 390. Accordingly, the sensory stimulation system 300 can receive user inputs to adjust the parameters of or deactivate some or all of the output systems 390 (560).

In response to the user inputs, the sensory stimulation system 300 can adjust the parameters of the specified output systems 390 or deactivate selected systems 390 accordingly (565). For example, a rider may wish to decrease the sensitivity of the seat response system 397 to reduce the amount of pitch or roll of the seats when stimulation commands 322 are executed. The rider may wish to increase the intensity of the haptic system to provide stronger vibrational feedback indicating upcoming maneuvers. As another example, the rider may wish to deactivate the audio outputs altogether to, for example, listen to music or a radio program. The sensory stimulation system 300 can provide a user interface to enable the rider to make adjustments and/or deactivate one or more of the output systems 390 accordingly.

Furthermore, the above-discussed operations in connection with FIGS. 5A and 5B make be repeated and/or performed dynamically for each maneuver performed by the AV control system 305 and/or each motion action experienced by the AV 200.

Hardware Diagram

Figure 6:
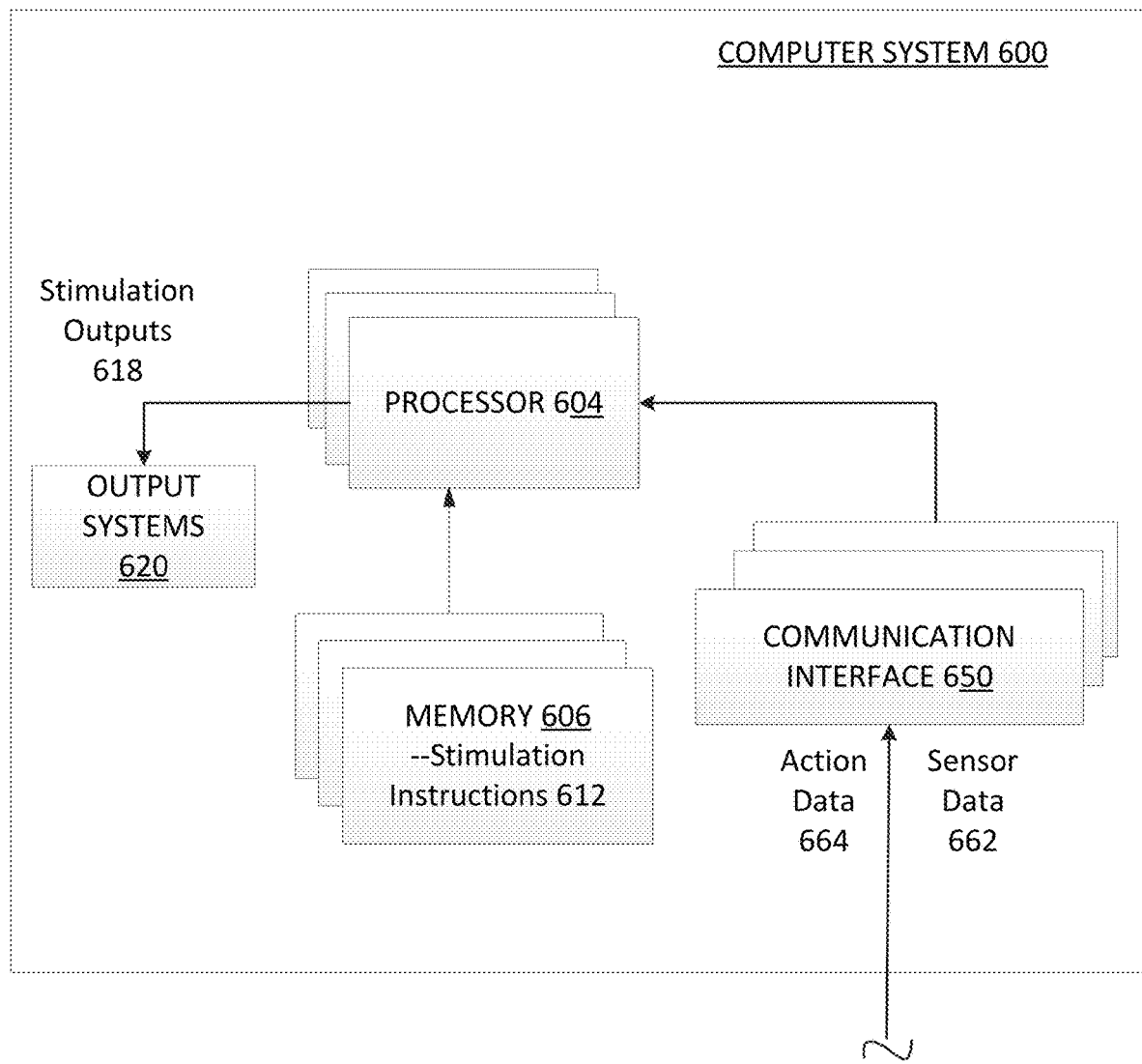
FIG. 6 is a block diagram illustrating a computer system upon which examples described herein may be implemented.

FIG. 6 is a block diagram illustrating a computer system upon which examples described herein may be implemented. For example, the intention signaling system 235, 300 shown and described with respect to FIGS. 2 and 3 may be implemented on the computer system 600 of FIG. 6. The computer system 600 can be implemented using one or more processors 604, and one or more memory resources 606. In the context of FIGS. 2 and 3, the sensory stimulation system 235, 300 can be implemented using one or more components of the computer system 600 shown in FIG. 6.

According to some examples, the computer system 600 may be implemented within an autonomous vehicle with software and hardware resources such as described with examples of FIGS. 1 through 3. In an example shown, the computer system 600 can be distributed spatially into various regions of the autonomous vehicle, with various aspects integrated with other components of the autonomous vehicle itself. For example, the processors 604 and/or memory resources 606 can be provided in the trunk of the autonomous vehicle. The various processing resources 604 of the computer system 600 can also execute stimulation instructions 612 using microprocessors or integrated circuits. In some examples, the stimulation instructions 612 can be executed by the processing resources 604 or using field-programmable gate arrays (FPGAs).

In an example of FIG. 6, the computer system 600 can include a local communication interface 650 (or series of local links) to vehicle interfaces and other resources of the autonomous vehicle (e.g., the computer stack drives). In one implementation, the communication interface 650 provides a data bus or other local links to electro-mechanical interfaces of the vehicle, such as wireless or wired links to the AV control system 220, 305.

The memory resources 606 can include, for example, main memory, a read-only memory (ROM), storage device, and cache resources. The main memory of memory resources 606 can include random access memory (RAM) or other dynamic storage device, for storing information and instructions which are executable by the processors 604. The processors 604 can execute instructions for processing information stored with the main memory of the memory resources 606. The main memory 606 can also store temporary variables or other intermediate information which can be used during execution of instructions by one or more of the processors 604. The memory resources 606 can also include ROM or other static storage device for storing static information and instructions for one or more of the processors 604. The memory resources 606 can also include other forms of memory devices and components, such as a magnetic disk or optical disk, for purpose of storing information and instructions for use by one or more of the processors 604.

According to some examples, the memory 606 may store a plurality of software instructions including, for example, stimulation instructions 612. The stimulation instructions 612 may be executed by one or more of the processors 604 in order to implement functionality such as described with respect to the sensory stimulation system 235, 300 of FIGS. 2 and 3.

In certain examples, the computer system 600 can receive sensor data 662 over the communication interface 650 from various AV subsystems 660 (e.g., the AV control system 220, 305 or an on-board computer 210 respectively). Additionally or alternatively, the computer system can receive action data 664 corresponding to acceleration, braking, and steering inputs to be performed by the AV control system 220, 305. In executing the stimulation instructions 612, the processing resources 604 can monitor the sensor data 662 and/or the action data 664 and generate stimulation outputs to the interior output systems 620 of the AV 200 in accordance with examples described herein.

It is contemplated for examples described herein to extend to individual elements and concepts described herein, independently of other concepts, ideas or systems, as well as for examples to include combinations of elements recited anywhere in this application. Although examples are described in detail herein with reference to the accompanying drawings, it is to be understood that the concepts are not limited to those precise examples. As such, many modifications and variations will be apparent to practitioners skilled in this art. Accordingly, it is intended that the scope of the concepts be defined by the following claims and their equivalents. Furthermore, it is contemplated that a particular feature described either individually or as part of an example can be combined with other individually described features, or parts of other examples, even if the other features and examples make no mentioned of the particular feature. Thus, the absence of describing combinations should not preclude claiming rights to such combinations.

What is claimed is:

1. A sensory stimulation system within an interior of an autonomous vehicle (AV), the sensory stimulation system comprising:
 a display system;
 one or more processors; and
 one or more memory resources storing instructions that, when executed by the one or more processors, causes the sensory stimulation system to:
  obtain maneuver data representing one or more maneuvers to be performed by the AV;
  for each respective maneuver of the one or more maneuvers, determine one or more visual outputs to provide a passenger of the AV with a sensory indication of the respective maneuver; and
  output the one or more visual outputs via the display system.

2. The sensory stimulation system of claim 1, wherein the one or more maneuvers comprise acceleration, braking, and change of direction actions to be executed by the AV.

3. The sensory stimulation system of claim 1, wherein the executed instructions further cause the sensory stimulation system to:

output a live presentation on the display system, the live presentation presenting the AV operating along a current route.

4. The sensory stimulation system of claim 3, wherein the live presentation comprises LIDAR data from at least one LIDAR sensor of the AV, the LIDAR data providing a sensor view of a surrounding environment of the AV.

5. The sensory stimulation system of claim 3, wherein the live presentation comprises live video data from one or more cameras of the AV.

6. The sensory stimulation system of claim 5, wherein the executed instructions cause the sensory stimulation system to display the live presentation by generating augmented reality features presented on the live video data, the augmented reality features representing actual features in a surrounding environment of the AV.

7. The sensory stimulation system of claim 6, wherein the augmented reality features comprise (i) an augmented reality representation of the AV traveling along a current route, and (ii) augmented reality representations of proximate external entities to the AV.

8. The sensory stimulation system of claim 7, wherein the proximate external entities comprise proximate pedestrians and proximate vehicles to the AV.

9. The sensory stimulation system of claim 3, wherein the live presentation includes a live map indicating route information of a current route traveled by the AV.

10. The sensory stimulation system of claim 1, wherein the executed instructions cause the sensory stimulation system to output the one or more visual outputs via the display system as preemptive visual indications of each of the one or more maneuvers, the preemptive visual indications of each maneuver being displayed prior to the maneuver being executed.

11. An autonomous vehicle (AV) comprising:
a sensor system to generate sensor data indicating a surrounding environment of the AV;
a display system;
acceleration, steering, and braking systems; and
a control system comprising one or more processing resources executing instructions that cause the control system to:
obtain maneuver data representing one or more maneuvers to be performed by the AV;
for each respective maneuver of the one or more maneuvers, determine one or more visual outputs to provide a passenger of the AV with a sensory indication of the respective maneuver; and
output the one or more visual outputs via the display system.

12. The AV of claim 11, wherein the one or more maneuvers comprise acceleration, braking, and change of direction actions to be executed by the AV.

13. The AV of claim 11, wherein the executed instructions further cause the control system to:
output a live presentation on the display system, the live presentation presenting the AV operating along a current route.

14. The AV of claim 13, wherein the sensor system comprises at least one LIDAR sensor, and wherein the live presentation comprises LIDAR data from the at least one LIDAR sensor of the AV, the LIDAR data providing a sensor view of the surrounding environment of the AV.

15. The AV of claim 13, wherein the sensor system comprises one or more cameras, and wherein the live presentation comprises live video data from the one or more cameras.

16. The AV of claim 15, wherein the executed instructions cause the control system to display the live presentation by generating augmented reality features presented on the live video data, the augmented reality features representing actual features in the surrounding environment of the AV.

17. The AV of claim 16, wherein the augmented reality features comprise (i) an augmented reality representation of the AV traveling along a current route, and (ii) augmented reality representations of proximate external entities to the AV.

18. The AV of claim 17, wherein the proximate external entities comprise proximate pedestrians and proximate vehicles to the AV.

19. The AV of claim 11, wherein the executed instructions cause the control system to output the one or more visual outputs via the display system as preemptive visual indications of each of the one or more maneuvers, the preemptive visual indications of each maneuver being displayed prior to executing the maneuver.

20. A non-transitory computer readable medium storing instructions for providing sensory stimulation for one or more riders to indicate motion of an autonomous vehicle (AV), wherein the instructions, when executed by one or more processors, cause the one or more processors to:
obtain maneuver data representing one or more maneuvers to be performed by the AV;
for each respective maneuver of the one or more maneuvers, determine one or more visual outputs to provide a passenger of the AV with a sensory indication of the respective maneuver; and
output the one or more visual outputs via a display system of the AV.

* * * * *